(12) United States Patent
Chu

(10) Patent No.: US 9,138,305 B2
(45) Date of Patent: Sep. 22, 2015

(54) IMPLANTS AND METHODS OF SECURING THE SAME

(75) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 207 days.

(21) Appl. No.: 13/164,220

(22) Filed: Jun. 20, 2011

(65) Prior Publication Data

US 2011/0319704 A1    Dec. 29, 2011

Related U.S. Application Data

(60) Provisional application No. 61/358,218, filed on Jun. 24, 2010.

(51) Int. Cl.
*A61F 2/00* (2006.01)
*A61F 2/02* (2006.01)

(52) U.S. Cl.
CPC .......... *A61F 2/0045* (2013.01); *A61F 2250/006* (2013.01)

(58) Field of Classification Search
CPC ................ A61B 2017/00805; A61F 2/0004; A61F 2/0031; A61F 2/0036; A61F 2/0045; A61F 2/0063; A61F 2002/0063
USPC ...................................... 600/30, 37; 606/151
See application file for complete search history.

(56) References Cited

U.S. PATENT DOCUMENTS

| | | | |
|---|---|---|---|
| 2005/0027220 A1 | 2/2005 | Wagner et al. | |
| 2005/0234291 A1* | 10/2005 | Gingras | 600/30 |
| 2006/0229596 A1* | 10/2006 | Weiser et al. | 606/37 |
| 2006/0260618 A1* | 11/2006 | Hodroff et al. | 128/830 |
| 2007/0162120 A1* | 7/2007 | Bouffier | 623/11.11 |
| 2008/0081945 A1* | 4/2008 | Toso et al. | 600/37 |
| 2008/0082121 A1* | 4/2008 | Chu | 606/205 |
| 2009/0171140 A1* | 7/2009 | Chu | 600/37 |

FOREIGN PATENT DOCUMENTS

| WO | 2009017680 A2 | 2/2009 | |
| WO | WO 2009038781 A1 * | 3/2009 | ............... A61F 2/00 |
| WO | 2010028242 A1 | 3/2010 | |

OTHER PUBLICATIONS

International Search Report and Written Opinion for International Application No. PCT/US2011/041251, mailed Sep. 14, 2011, 15 pages.

* cited by examiner

*Primary Examiner* — Jacqueline Cheng
*Assistant Examiner* — Kaylee Wilson
(74) *Attorney, Agent, or Firm* — Brake Hughes Bellermann LLP

(57) ABSTRACT

In one embodiment, an implant includes a support member defining an opening and a strap being configured to extend through the opening defined by the support member. The strap includes a first retention member and a second retention member. The first retention member is configured to engage the support member to couple the strap to the support member. The second retention member being configured to engage bodily tissue of a patient to couple the strap to the bodily tissue. In another embodiment, an implant includes a support member defining an opening and a strap defining an opening. The strap is configured to be coupled to the support member and to bodily tissue of a patient. The strap is configured to extend through the opening defined by the support member and the opening defined by the strap.

19 Claims, 11 Drawing Sheets

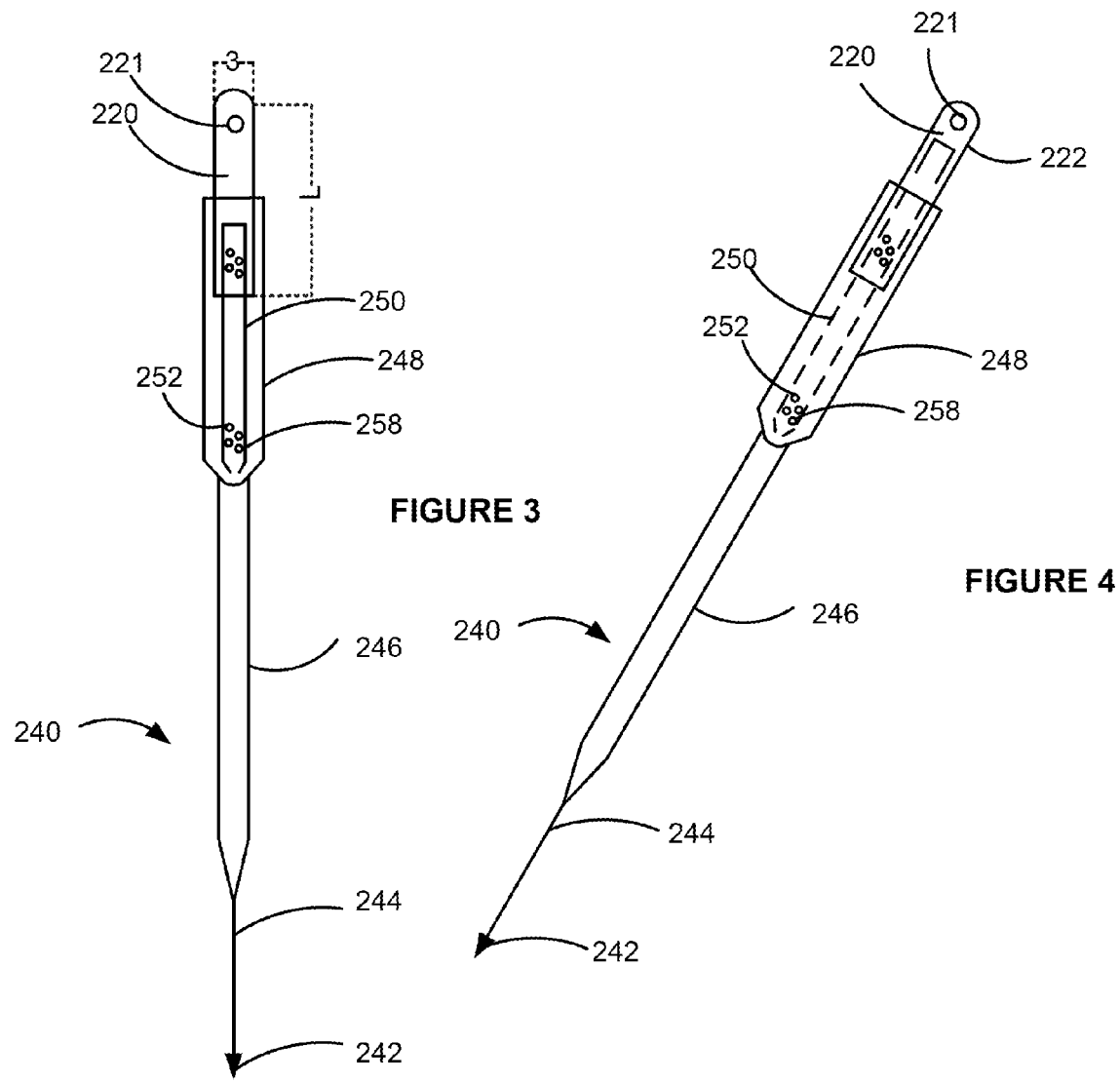

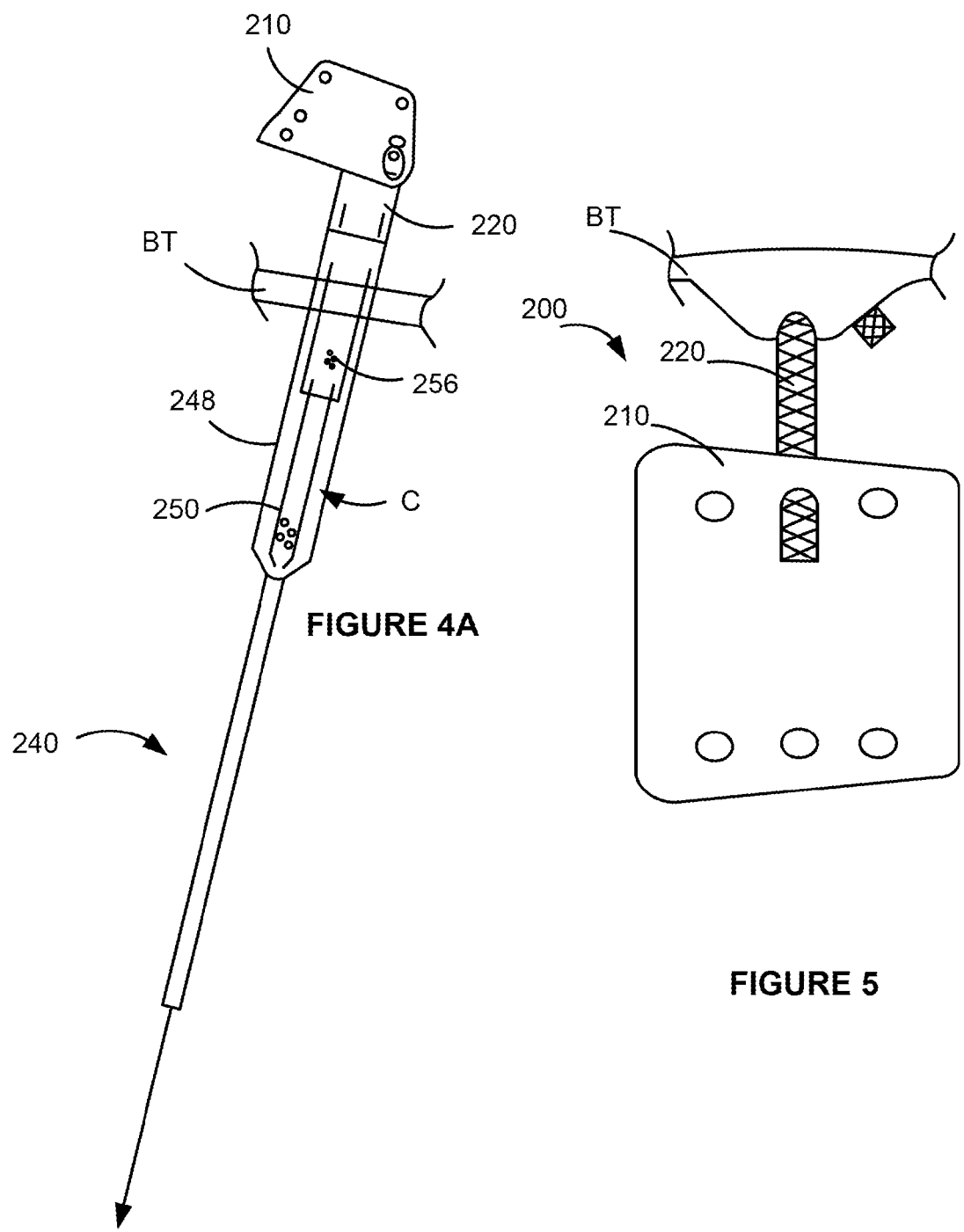

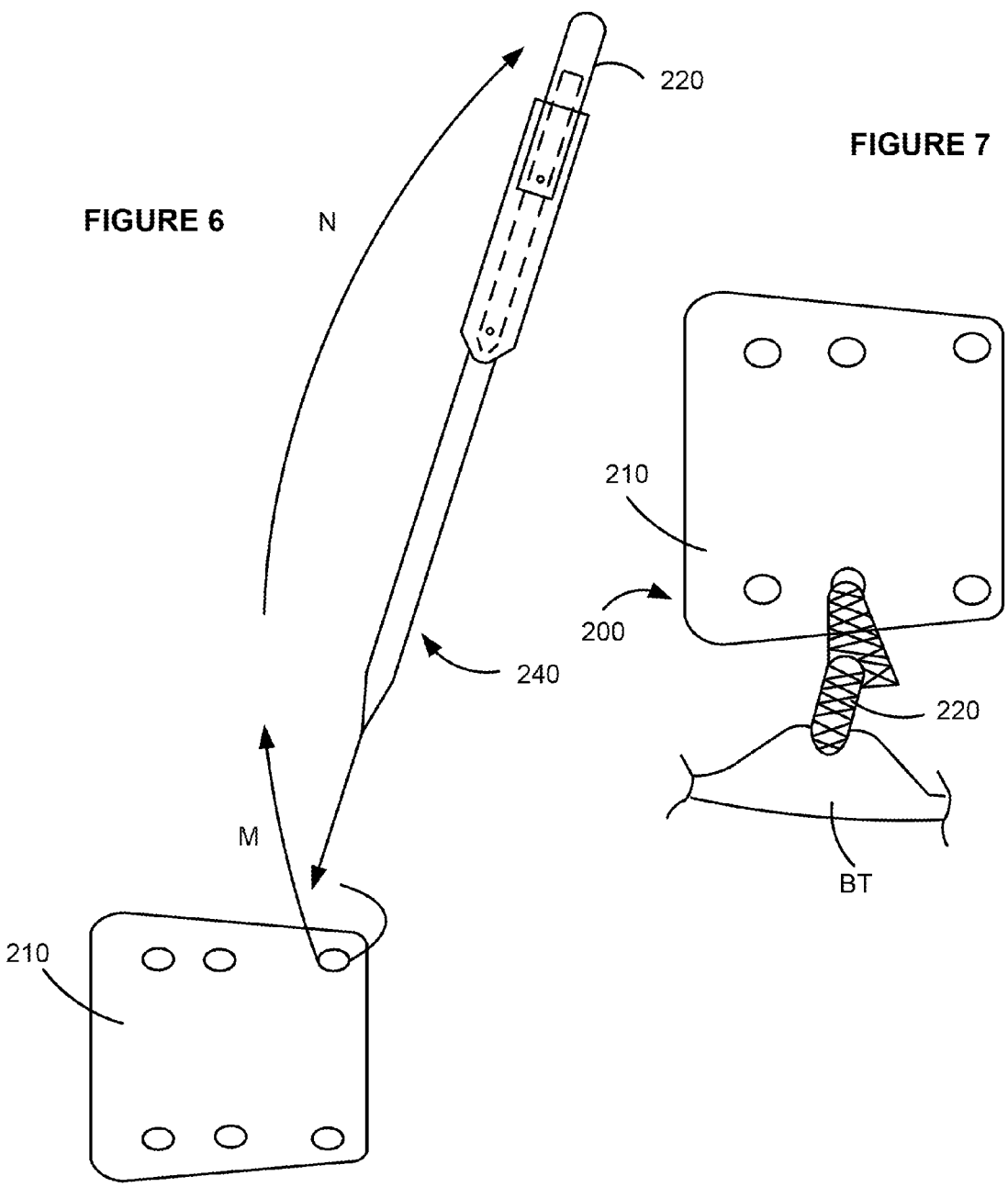

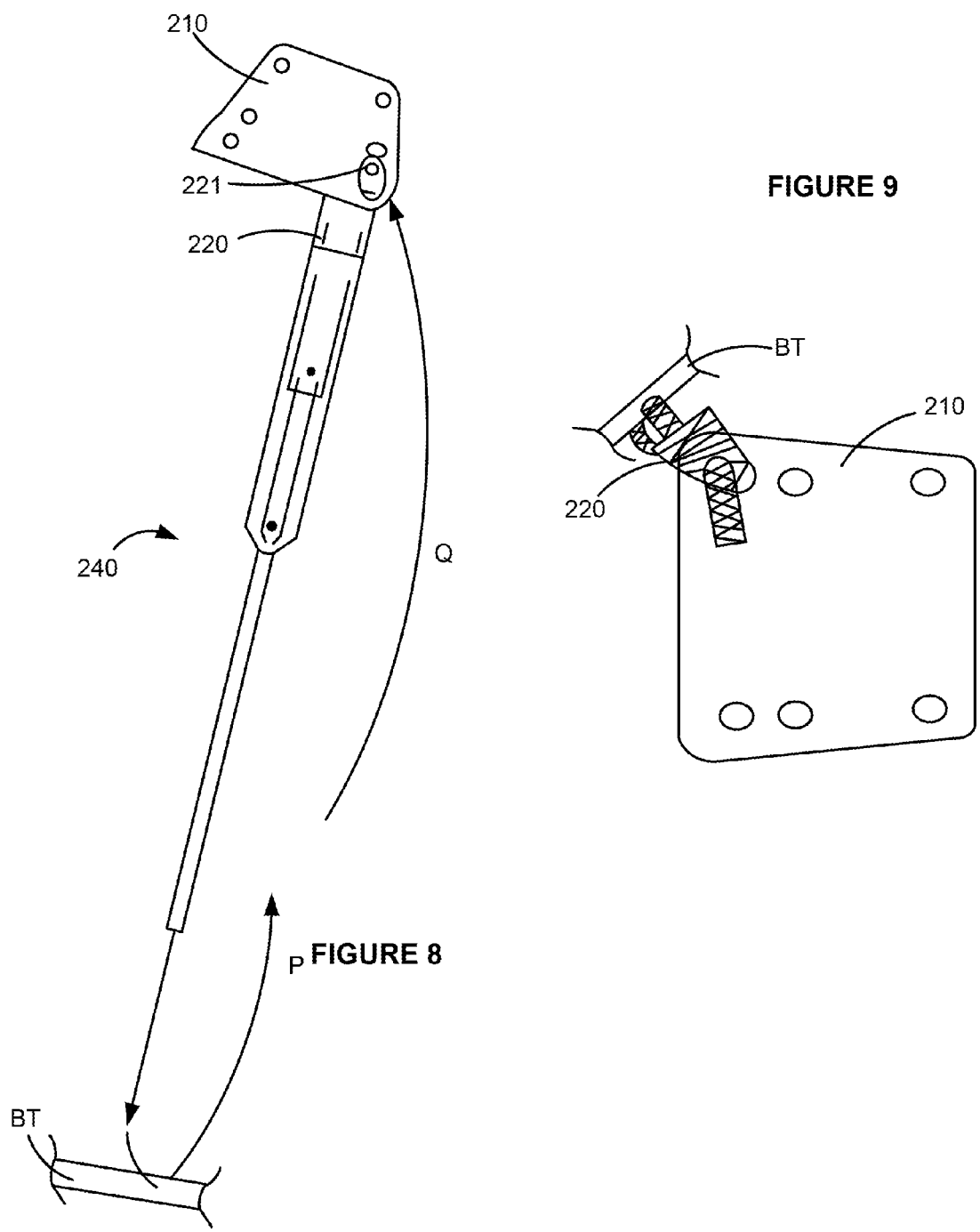

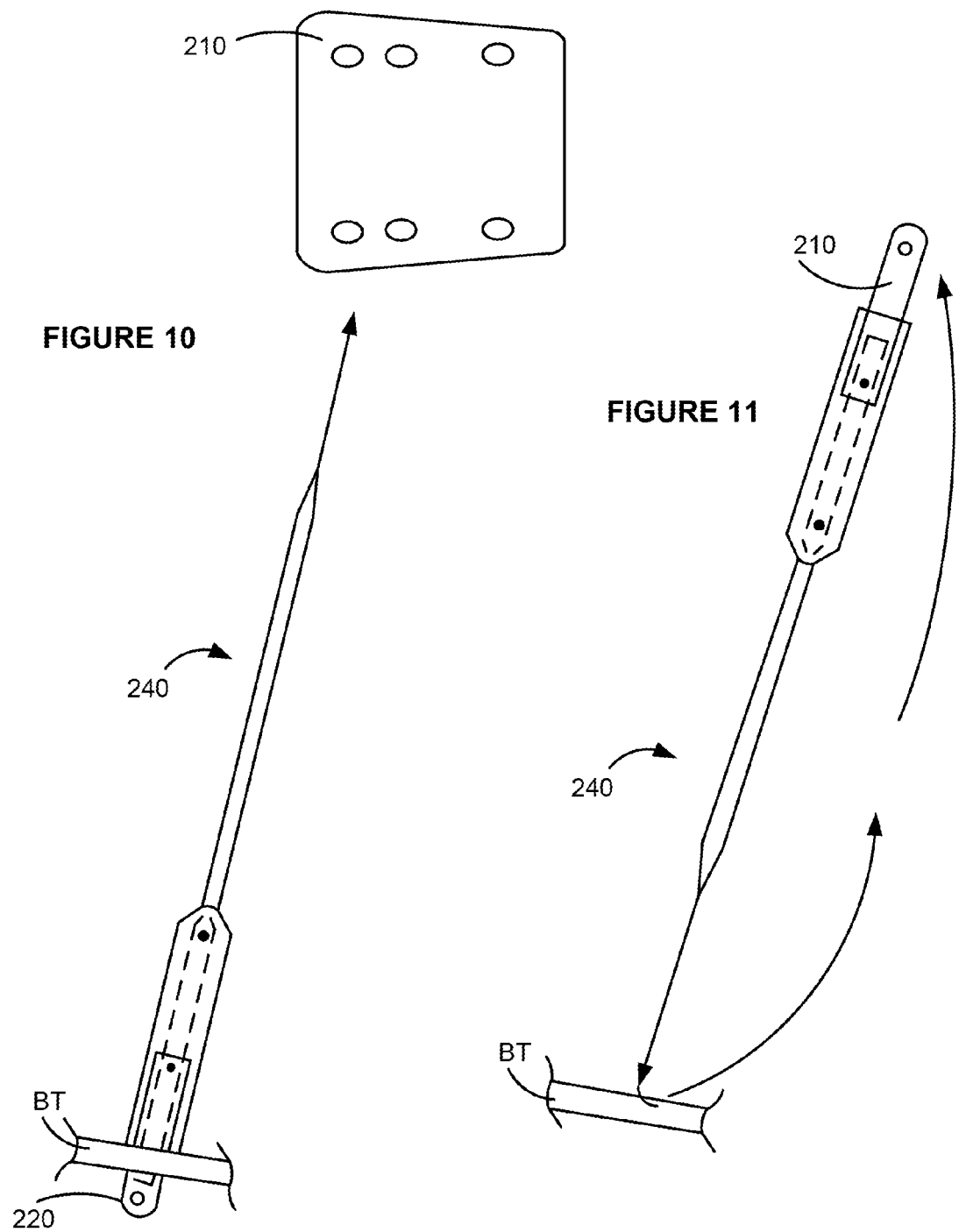

IMPLANTS AND METHODS OF SECURING THE SAME

RELATED APPLICATION

This application is claims priority to U.S. Patent Application No. 61/358,218, filed Jun. 24, 2010, entitled "IMPLANTS AND METHODS OF SECURING THE SAME," which is incorporated by reference herein in its entirety.

TECHNICAL FIELD

This disclosure relates generally to medical devices and more particularly to implants configured to provide support within a body of a patient and methods for securing such implants with the body of the patient.

BACKGROUND

A variety of medical procedures are performed to treat various female pelvic dysfunctions, including procedures to treat urinary incontinence, and correcting various prolapse conditions such as uterine prolapse, cystoceles, rectoceles, and vaginal vault prolapse.

Women often experience vaginal prolapses due to age or other factors. For example, women may experience a cystocele, a rectocele and/or a hysterocele. A cystocele occurs when the bladder bulges into the vagina, and a rectocele occurs when the rectum bulges into the vagina. A hysterocele occurs when the uterus descends into the vagina. An enterocele (small bowel prolapse) can also occur, when the small bowel pushes through the upper wall of the vagina.

Treatments of such dysfunctions have included suturing procedures or the use of implants for support or suspension. A hysterocele is often treated with a hysterectomy followed by a vaginal vault suspension. Various devices and procedures are used to deliver and secure pelvic implants within a variety of different anatomical structures within a pelvic region. Implants can be delivered to a pelvic region through one or more vaginal incisions, and/or through exterior incisions in the patient.

Existing implants differ in many ways including size, shape, material, number and location of straps, and in the method in which they are delivered and placed within a pelvic region. Additionally, depending on the particular condition to be treated and the implant used, pelvic floor repair can require various fixation locations within a pelvic region. For example, an implant can be secured using a number of fixation points.

Sutures may be used to bridge, anchor and suspend the implant in place within the body of the patient. Sutures, however, may not provide enough surface area for tissue in-growth and may require knotting in order to be secured. Alternatively, implants formed with mesh straps can provide for tissue in-growth and the width of the mesh can help prevent tissue cutting.

Various complications can occur during a procedure to deliver and secure a pelvic implant due to many factors. Thus, it would be desirable to provide improved pelvic implants and delivery processes associated with such implants that facilitate the delivery of the implant into the body of the patient.

SUMMARY

In one embodiment, an implant includes a support member defining an opening and a strap being configured to extend through the opening defined by the support member. The strap includes a first retention member and a second retention member. The first retention member is configured to engage the support member to couple the strap to the support member. The second retention member being configured to engage bodily tissue of a patient to couple the strap to the bodily tissue. In another embodiment, an implant includes a support member defining an opening and a strap defining an opening. The strap is configured to be coupled to the support member and to bodily tissue of a patient. The strap is configured to extend through the opening defined by the support member and the opening defined by the strap.

BRIEF DESCRIPTION OF THE DRAWINGS

FIGS. 3 and 4 are top and perspective views, respectively, of the strap of the implant of FIG. 2 coupled to a delivery assembly.

FIG. 4A illustrates the strap of the implant of FIG. 2 and the delivery assembly of FIGS. 3 and 4 extending through bodily tissue.

FIG. 5 illustrates the implant of FIG. 2 coupled to bodily tissue.

FIG. 6 illustrates the strap of the implant FIG. 2 and the delivery assembly of FIGS. 3 and 4 and the support member of the implant of FIG. 2.

FIG. 7 illustrates the implant of FIG. 2 coupled to bodily tissue.

FIG. 8 illustrates the strap of the implant FIG. 2 and the delivery assembly of FIGS. 3 and 4 extending through the support member of the implant of FIG. 2 and being inserted into bodily tissue.

FIG. 9 illustrates the implant of FIG. 2 coupled to bodily tissue.

FIG. 10 illustrates the strap of the implant FIG. 2 and the delivery assembly of FIGS. 3 and 4 extending through bodily tissue and the support member of the implant of FIG. 2.

FIG. 11 illustrates the strap of the implant of FIG. 2 and the delivery assembly of FIGS. 3 and 4 being inserted into bodily tissue.

DETAILED DESCRIPTION

Figure 1:
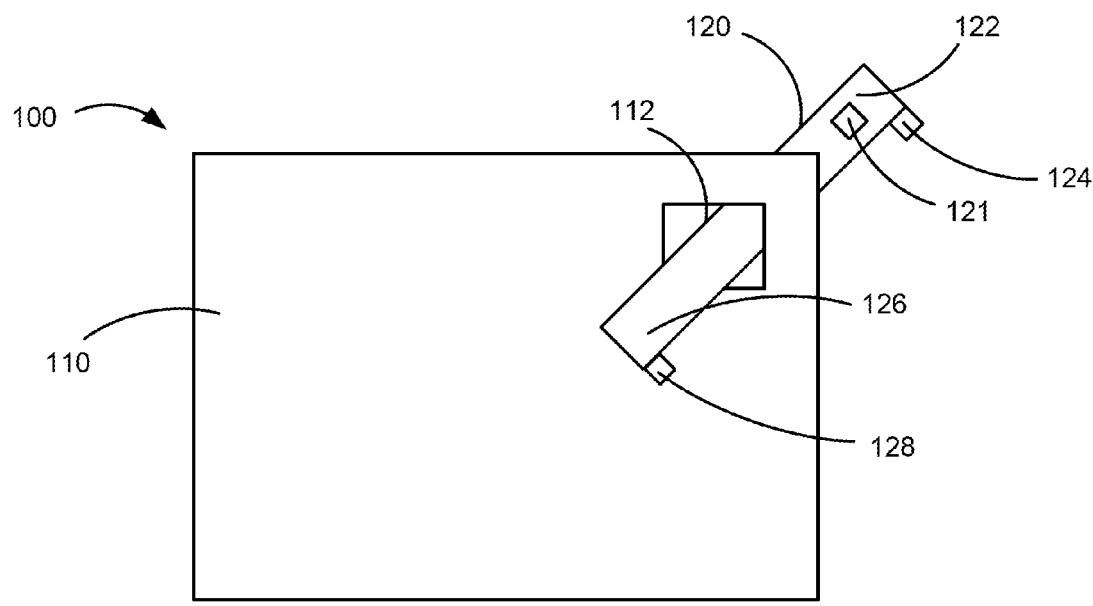
FIG. 1 is a schematic illustration of an implant according to an embodiment of the invention.

The devices and methods described herein are generally directed to implants (e.g., posterior support implants, anterior support implants, total pelvic floor repair implants, incontinence sling implants (FIG. 15)) and the delivery and placement of such implants within a pelvic region (also referred to herein as "pelvis") of a patient. An implant can be placed into the pelvic space of a patient and secured at any of several locations within the pelvic space to treat many different female or male pelvic floor dysfunctions. For example, in a female patient an implant can be secured to a sacrospinous ligament or a ureterosacral ligament for uterine preservation (e.g., if a prolapsed uterus is otherwise healthy, a hysterectomy is not preformed and the uterus is re-suspended with an implant), or for posterior support. In another embodiment, an implant can be secured to pubo-urethral tissue or an obturator muscle (e.g., internus or externus) or membrane (each also referred to herein as "obturator") to treat, for example, incontinence. In yet another embodiment, an implant can be secured to a sacrospinous ligament or an arcus tendineus fascia pelvis (i.e., white line) (also referred to herein as "arcus tendineus") for paravaginal repairs including, for example, cystoceles, rectoceles and enteroceles. An implant can also be secured to various combinations of such locations. A single implant or multiple implants can be used in a single procedure. In some applications, when multiple implants are used, support can be provided in desired areas and improved control of the direction of stretch or support of the implant can be achieved. Various delivery devices, delivery aids, and methods are also described for delivering and securing an implant assembly within the patient.

An implant according to an embodiment of the invention can be implanted, for example, through a vaginal incision, in a retro-pubic direction (behind the pubic bone), or in a pre-pubic direction (in front of the pubic bone). In other embodiments, an implant can be placed in the direction of other anatomical structures as desired. A procedure to deploy a pelvic implant can include vaginal incisions, such as an anterior vaginal incision and/or an anterior vaginal incision. In some embodiments, a procedure may include an exterior incision.

Various embodiments of implants are described herein. An implant can be delivered to a pelvic region of a patient using a variety of different delivery devices, only some examples of which are described herein. Various delivery aids are also described, some of which can be included as part of an implant (e.g., provided to a physician assembled) some of which can be assembled to an implant just prior to implantation. Such delivery aids are typically removed after placing one or more straps of an implant at a desired tissue securement location, leaving the strap to engage the tissue and support the support portion of the implant. For example, a sleeve or dilator assembly can be used to lead an implant or a strap of an implant through a tissue in an intracorporeal location (i.e., within the patient's body), such as the sacrospinous ligament or arcus tendineus. In other embodiments, a sleeve or dilator assembly can be used to lead an implant or a strap of an implant through a tissue and to an extracorporeal location (outside the patient's body), such as through an obturator membrane or muscle and out through the skin of the patient.

In some embodiments, an implant can be associated to delivery aid, such as a sleeve assembly or dilator device, after such delivery aid has been placed within a pelvic region. For example, in an embodiment of an implant having multiple straps, prior placement of a delivery aid can help with coordinating and organizing the placement of the various straps. Placing a delivery aid within a pelvic region first also helps reduce handling of the implant which can reduce damage to the implant during an implantation procedure.

As used herein, the terms proximal portion or proximal end refer to the portion or end, respectively, of a device that is closest to a physician when performing a medical procedure, and the terms distal portion or distal end refer to the portion or end, respectively, of the device that is furthest from the physician during a medical procedure. For example, a distal end or portion of a sleeve assembly or dilator device as described herein refers to the end or portion of the device that is first inserted into a body of a patient during a medical procedure. The proximal end or portion is the end or portion of the device that is inserted into a body of the patient after the distal end or distal portion. The terms "trailing end" and "leading end" are also referred to herein and have similar meanings as proximal and distal, respectively. As used herein, the term "leading end" refers to the end of a device or apparatus that is inserted into a body first. The term "trailing end" refers to the end of the device or apparatus that is inserted into the body after the leading end.

FIG. 1 is a schematic illustration of an implant 100 according to an embodiment. The implant 100 includes a support member 110 and a strap 120. The support member 110 defines an opening 112. The strap 120 includes a distal end portion 122 and a proximal end portion 126. The strap 120 includes a first retention member 128 and a second retention member 124. Although only one strap 120 is illustrated and described, the implant 100 may include any number of straps. For example, in one embodiment, the implant 100 includes four straps 120. In other embodiments, the implant includes six straps 120.

The support member 110 is configured to be placed and secured within a body of a patient. The support member 110 is configured to provide support to a portion of the body. For example, in some embodiments, the support member 110 may be placed and secured proximate the bladder of the patient to provide support to the bladder of the patient. In other embodiments, the support member 110 is configured to be placed and secured proximate the uterus of the patient to provide support to the uterus of the patient. In further embodiments, the support member 110 is configured to be placed and secured at other locations within the body of the patient.

The strap 120 is configured to extend through the opening 112 defined by the support member 110. The first retention member 128 is configured to contact or engage the support member 110 to couple the strap 120 to the support member 110. The second retention member 126 is configured to contact or engage bodily tissue (such as a portion of the sacrospinous ligament, arcus tendineus, or the obturator membrane of the patient). In one embodiment, the first retention member 128 is disposed proximate the proximal end portion 126 of the strap 120. Similarly, in one embodiment, the second retention member 124 disposed proximate the distal end portion 122 of the strap 120.

In one embodiment the first retention member 128 extends away from a longitudinal axis defined by the strap 120. For example, in one embodiment the first retention member 128 is a tang. In another embodiment, the first retention member 128 is a set or a plurality of tangs. In such embodiments, the tang or tangs are configured to engage the support member 110 to couple the strap 120 to the support member 110. The terms "tanged" or "tangs" as used herein mean roughened or jagged edges or areas, such as can result from cutting a woven or knit mesh material. In some embodiments, the first retention member 128 is a set or plurality of reinforced tangs. In such embodiments, the tangs include reinforcement material. In some embodiments, the reinforcement material is polypropylene.

In some embodiments, the first retention member 128 and the strap 120 are monolithically or unitarily formed. In other words, the first retention member 128 and the strap 120 are made of a single piece of material. In other embodiments, the first retention member 128 and the strap 120 are made of different pieces of material and are coupled together.

In one embodiment the second retention member 124 extends away from a longitudinal axis defined by the strap 120. For example, in one embodiment the second retention member 124 is a tang. In another embodiment, the first retention member 124 is a set or a plurality of tangs. In such embodiments, the tang or tangs are configured to engage bodily tissue of the patient to couple the strap 120 (and the support member 110) to the bodily tissue. In some embodiments, the second retention member 124 is a set or plurality of reinforced tangs. In such embodiments, the tangs include a reinforcement material.

In some embodiments, the second retention member 124 and the strap 120 are monolithically or unitarily formed. In other words, the second retention member 124 and the strap 120 are made of a single piece of material. In other embodiments, the second retention member 124 and the strap 120 are made of different pieces of material and are coupled together.

In some embodiments, the strap 120 defines an opening 121. The opening 121 is configured to receive a portion of the strap 120 such that the strap 120 extends through the opening 121. In some embodiments, the opening 121 defined by the strap 120 is configured to engage the portion of the strap 120 that extends through the opening 121 to couple the portion of the strap 120 that defines the opening 121 to the portion of the strap 120 that extends through the opening. For example, in some embodiments, the portion of the strap 120 that defines the opening 121 frictionally couples to the portion of the strap 120 that extends through the opening 121. In other embodiments, one or both of the portion of the strap 120 that defines the opening 121 and the portion of the strap 120 that extends through the opening 121 include a coupling structure to couple the portion of the strap 120 that defines the opening 121 to the portion of the strap 120 that extends through the opening 121.

Accordingly, as will be described in more detail below, the strap 120 can extend through bodily tissue and then through the opening 121 to secure the strap 120 to the bodily tissue. Alternatively, the strap 120 can extend through the opening 112 defined by the support member 110 and then through the opening 121 to secure the strap 120 to the support member 110. In a further alternative, the strap can extend through the opening 112 defined by the support member 110, through the bodily tissue, and then through the opening 121 defined by the strap 120 to secure the strap 120 to the support member 110 and the bodily tissue.

In some embodiments, the opening 121 defined by the strap 120 is formed by cutting or slitting the strap 120. In some embodiments, the opening 121 defined by the strap 120 includes a molded portion. The molded portion may include a material that is different than the material of the strap. In some embodiments, the strap and the molded portion are made of polypropylene. In other embodiments, the strap is made from an absorbable thread such as polyioxanne or polyglycolic. In some embodiments, the molded portion includes extension members or teeth that are configured to engage the portion of the strap 120 that extends through the opening 121 to help secure the portion of the strap 120 that extends through the opening 121 to the portion of the strap 120 that defines the opening 121.

In some embodiments, the strap 120 includes a loop (not illustrated) that extends from the strap 120. For example, in some embodiments the loop is a suture loop. The strap 120 may extend through the loop to help secure the strap 120 to the support member 110, the bodily tissue, or both.

The support member 110 may be of any shape. In some embodiments, the support member 110 is shaped to be inserted into a body of a patient and provide support for a portion of the body of the patient. For example, in some embodiments, the support member 110 is square. In other embodiments, the support member 110 is rectangular.

The strap 120 may be of any shape. In some embodiments, the strap 120 is shaped to be inserted into a body of a patient and be coupled to the support member 110 and to bodily tissue. In some embodiments, the strap 120 is rectangular. In some embodiments, the strap 120 includes rounded portions.

The support member 110 and the strap 120 may be formed of any biocompatible materials. In some embodiments, the support member 110 and the strap 120 are formed of the same materials. In other embodiments, the support member 110 and the strap 120 are formed of different materials. For example, in one embodiment, the support member 110 is formed of a bovine Xenform® as sold by Boston Scientific Corporation or cadaveric tissue Repliform® (human dermic) as sold by Boston Scientific and the strap 120 is formed of a mesh material. For example, the strap 120 may be formed of Advantage® mesh or the Polyform™ synthetic mesh, both as sold by Boston Scientific Corporation. In some embodiments, in the strap 120 may be formed of a polymer material. In some embodiments, the strap 120 is made of polypropylene. In other embodiments, the strap 120 is made of an absorbable material. In some embodiments, the mesh material of the strap 120 allows for tissue in-growth to secure the implant 100 to the bodily tissue of the patient. In some embodiments, the support member 110 is formed of a mesh material.

Figure 2:
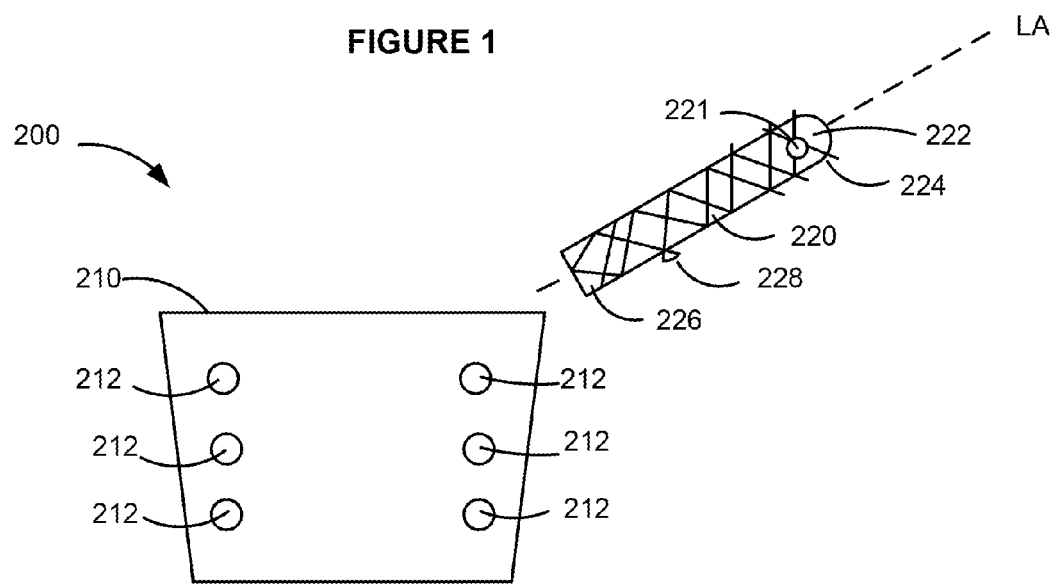
FIG. 2 is a top view of an implant according to an embodiment of the invention.

FIG. 2 is a top view of an implant 200 according to an embodiment. The implant includes a support member 210 and a strap 220. The support member 210 defines openings 212. The strap 220 includes a distal end portion 222 and a proximal end portion 226. The strap 220 includes a first retention member 228 and a second retention member 224. Although only one strap 220 is illustrated and described, the implant 200 may include any number of straps.

The support member 210 is configured to be placed and secured within a body of a patient. The support member 210 is configured to provide support to a portion of the body. For example, in some embodiments, the support member 210 may be placed and secured proximate the bladder of the patient to provide support to the bladder of the patient. In other embodiments, the support member 210 is configured to be placed and secured proximate the uterus of the patient to provide support to the uterus of the patient. In further embodiments, the support member 210 is configured to be placed and secured at other locations within the body of the patient.

The support member 210 may define any number of openings 212. In the illustrated embodiment, the support member 210 defines six openings 212. The openings 212 may be placed in the support member 210 during the manufacture of the implant 200 or may be made by a physician prior to placing the implant 200 within the body of the patient. The openings 212 may be of any size and shape. For example, the openings 212 may be slits, round, oval, rectangular, square, or any other shape.

The strap 220 is configured to extend through an opening 212 defined by the support member 210. The first retention member 228 is configured to contact or engage the support member 210 to couple the strap 220 to the support member 210. The second retention member 226 is configured to contact or engage bodily tissue (such as a portion of the sacrospinous ligament or arcus tendineus of the patient). In one embodiment, the first retention member 228 is disposed proximate the proximal end portion 226 of the strap 220. Similarly, in one embodiment, the second retention member 224 disposed proximate the distal end portion 222 of the strap 220.

In the illustrated embodiment, the first retention member 228 and the second retention member 224 extend away from a longitudinal axis LA defined by the strap 220. In the illustrated embodiment, the first retention member 228 and the second retention member 224 are tangs or groups of tangs. In one embodiment, the tangs are formed when cutting the mesh material. In some embodiments, additional material is added to the tangs to provide strength to or reinforce the retention members. In the illustrated embodiment the tangs are only located near the end portions 222 and 226 of the strap 220. In other embodiments, the tangs are located along the entire length of the strap 220. In some embodiments, the tangs are located on both sides of the strap 220.

The strap 220 defines an opening 221. The opening 221 is configured to receive a portion of the strap 220 such that the strap 220 extends through the opening 221. In other embodiments, the strap defines more than one opening. In such embodiments, more than one strap may be coupled together before coupling the straps to the support member.

The strap 220 may be of any size or shape. As best illustrated in FIGS. 3 and 4, in the illustrated embodiment, the width W of the strap 220 is about one (1) cm and the length L of the strap 220 is about eight (8) cm. In other embodiments, the width W of the strap 220 is greater or less than one (1) cm. In other embodiments, the length L of the strap 220 is greater or less than eight (8) cm.

In some embodiments, a delivery assembly is used to assist in the delivery of the strap and the implant into the body of the patient. For example, in some embodiments, delivery assemblies as described in U.S. Patent Publication No. 2009/0171143, which is hereby incorporated by reference in its entirety, may be used.

FIGS. 3 and 4 illustrate the strap 220 coupled to a delivery assembly 240. The delivery assembly 240 may be used to assist in the delivery of the strap 220 into the body of the patient. In one embodiment, the delivery assembly 240 is configured to engage a delivery device to deliver the strap 220 and delivery assembly 240 into the body of the patient. For example, in one embodiment, the delivery device is configured to engage a Capio® device as sold by Boston Scientific Corporation. In other embodiments, the delivery assembly 240 is configured to be used with a different delivery device.

The delivery assembly 240 is configured to lead or guide the strap 220 into place within the body of the patient. Specifically, the delivery assembly 240 can be passed through bodily tissue of the patient and the strap 220, while coupled to the delivery assembly 240, can be pulled through such bodily tissue.

The delivery assembly 240 includes a needle 242 (such as a bullet needle), a leader 244, a dilator 246, a sleeve 248, a leader loop 250, and separators 252 and 254. The needle 242 is configured to pierce bodily tissue. The dilator 246 includes a taper and is configured to dilate the bodily tissue prior to entrance of the strap 220 into the bodily tissue. The sleeve 248 is configured to cover the retention members (i.e., the sets of tangs) 224 and 226 during the placement of the strap 220 in the bodily tissue. The leader loop 250 is a suture and is configured to couple the delivery assembly 240 to the strap 220. In the illustrated embodiment, the leader loop 250 is threaded through a portion of the strap 220 to couple the delivery assembly 240 to the strap 220. In some embodiments where the implant includes more than one strap, the dilators and leaders of the different straps are color coded so as to allow the physician the ability to distinguish the different assemblies and straps during the procedure.

As best illustrated in FIG. 4, in the illustrated embodiment, the sleeve 248 covers most of the strap 220, but does not cover end portion 222 of the strap 220. Specifically, to aid in the insertion of the strap 220 into the body of the patient, in the illustrated embodiment, the sleeve covers all but about three (3) cm of the length of the strap 220 (as discussed below). In other embodiments, a larger or short portion of the strap 220 is not covered by the sleeve 248. In some embodiments, the sleeve covers the entire strap 220.

In one embodiment, the strap 220 may be coupled to the support member 210 by threading the delivery assembly 240 (beginning with the needle 242) through one of the openings 212 defined by the support member 210. The delivery assembly 240 and strap 220 are then pulled through the opening 212 until the retention member 224 (the portion of the strap 220 that is disposed outside of the sleeve 248) engages the support member 210. The engagement of the retention member 224 with the support member 210 couples the strap 220 to the support member 210. In one embodiment, the implant 200 can then be inserted into the body of the patient. In another embodiment, another strap (not illustrated) can be coupled to the support member 210. In some embodiments, the delivery assembly 240 and strap 220 may be threaded through two of the openings 212 defined by the support member 210 to more securely couple the strap 220 to the support member 210. In other embodiments, the strap 220 may be sutured to the support member 210.

Once the strap 220 is coupled to the support member 210, a delivery device, such as a Capio® device sold by Boston Scientific Corporation, may be associated or otherwise coupled to the delivery assembly 240. The delivery assembly 240 may then be inserted into the relevant bodily tissue (such as the sacrospinous ligament of the patient) and pulled through the tissue. Once the strap 220 is appropriately placed within the bodily tissue, the delivery assembly 240 may be removed from the strap 220. As best illustrated in FIG. 4A, in one embodiment, the delivery assembly 240 may be removed by cutting (for example, at location C) a portion of the sleeve 248 and one portion of the leader loop 250. The separators 252 and 254 are configured keep the portions of the leader loop 250 separated to assist in the cutting of one portion of the leader loop 250. The delivery assembly may then be pulled away from the strap 220 leaving the strap placed within the body of the patient. In the illustrated embodiment, the delivery assembly also includes tacks 256 that couple the sleeve 248 to the strap 220. In such an embodiment, once the leader loop 250 is cut the pulling of the delivery assembly 240 breaks the tacks and frees the delivery assembly 240 from the strap 220. Accordingly, the strap 220 remains in place within the bodily tissue.

The strap 220 may be compressed or folded during the insertion of the strap 220 into the bodily tissue. For example, the strap 220 may be compressed or folded widthwise during the insertion of the strap 220. Once the strap 220 is placed, the strap 220 may uncompress or unfold to engage and secure to the bodily tissue. Additionally, the bodily tissue may collapse about the strap 220 to engage the strap 220 to couple the strap 220 to the bodily tissue once the delivery assembly 240 is removed.

As illustrated in FIG. 5, according to the above procedure, the strap 220 is coupled to the bodily tissue BT and to the support 210.

In one embodiment, as illustrated in FIGS. 6 and 7, to couple the strap 220 to the support member 210, the delivery assembly 240 and the strap 220 may be threaded through one of the openings 212 defined by the support member 210 and then threaded through the opening 221 defined by the strap 220. For example, as illustrated in FIG. 6 the delivery assembly 240 and strap 220 may be moved along route M to thread the delivery assembly 240 and strap 220 through an opening 212 defined by the support member 210 and then along route N to thread the delivery assembly 240 and the strap 220 through the opening 221 defined by the strap 220. Accordingly, the strap 210 is looped around a portion of the support member 210 to couple the strap 220 to the support member 210. In such an embodiment, the strap 210 is "looped coupled" to the support member 210. The delivery assembly 240 can then be passed through the relevant bodily tissue BT and removed from the strap 220 to couple the strap 220 to the bodily tissue BT as illustrated in FIG. 7.

In another embodiment, as illustrated in FIGS. 8 and 9, the delivery assembly 240 and strap 220 may be passed through one of the openings 212 defined by the support member 210. In one embodiment, the delivery assembly 240 and strap 220 are threaded through the opening 212 defined be the support member 210 outside of the body of the patient. The delivery assembly 240 and strap 220 may then be passed through the relevant bodily tissue BT. Finally, the delivery assembly 240 and strap 220 may be passed through the opening 221 defined by the strap 220. For example, as illustrated in FIG. 8, the delivery assembly 240 and strap 220 may be moved along route P to pass the delivery assembly 240 and the strap 220 through the bodily tissue BT and then the delivery assembly 240 and the strap 220 may be moved along route Q to thread the delivery assembly 240 and the strap 220 through the opening 221 defined by the strap 220. The delivery assembly 240 may then be removed from the strap 220. Thus, the strap 220 is looped around both the support member 210 and the bodily tissue BT as illustrated in FIG. 9.

In another embodiment, as illustrated in FIG. 10, the strap 220 may be inserted into the body of the patient prior to coupling the strap 220 to the support member 210. Specifically, in such an embodiment, the delivery assembly 240 may be associated or coupled to a delivery device and passed through the relevant bodily tissue (such as a sacrospinous ligament of the patient). The delivery assembly 240 and the strap 220 may then be pulled through the bodily tissue to appropriately place the strap 220 within the tissue. If the strap 220 is not appropriately placed, the delivery assembly 240 and strap 220 may be replaced into the tissue.

In some embodiments, the delivery assembly 240 is sufficiently long to extend to a location outside of the patient. The delivery assembly 240 and strap 220 can then be threaded through an opening 212 defined by the support member 210. The support member 210 can then be slid along the delivery assembly 240 and strap 220 until it reaches the appropriate location on the strap 220. The delivery assembly 240 can then be removed from the strap 220 to couple the support member 210 to the strap 220 and the strap to the bodily tissue.

Figure 12:
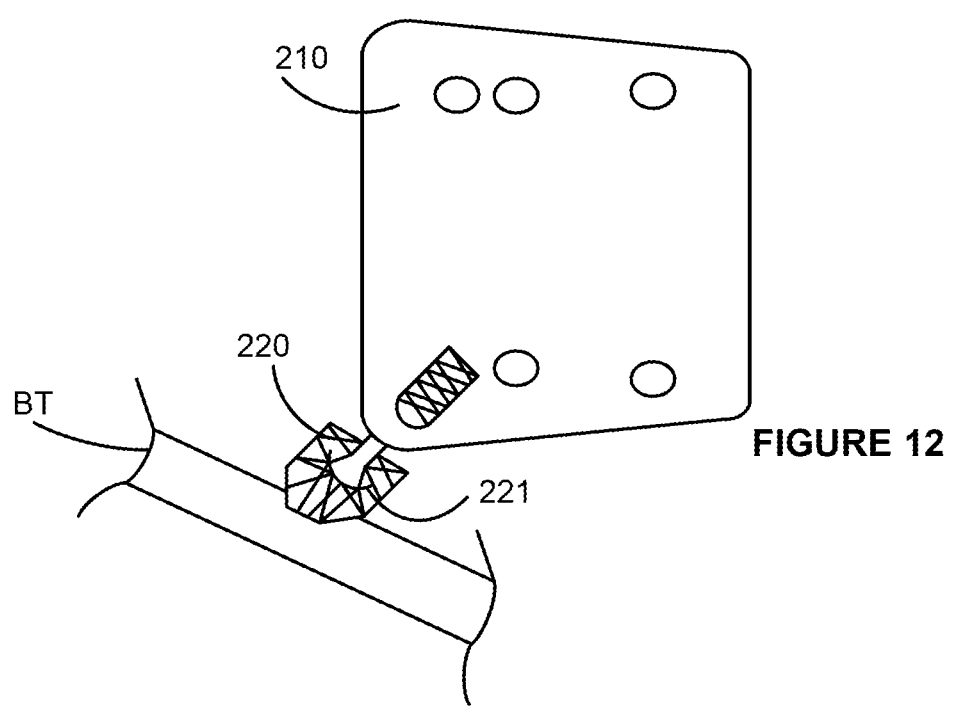
FIG. 12 illustrates the implant of FIG. 2 coupled to bodily tissue.

In one embodiment, as illustrated in FIGS. 11 and 12, the delivery assembly 240 may be associated or coupled to a delivery device and passed through the relevant bodily tissue BT. The delivery assembly 240 and strap 220 may then be pulled through the bodily tissue BT to appropriately place the strap 220 within the bodily tissue BT. For example, as illustrated in FIG. 11, the delivery assembly 240 and the strap 220 may be moved along route R to pass the delivery assembly 240 and the strap 220 through the bodily tissue BT. The delivery assembly 240 may then be removed from the delivery device and passed through the opening 221 defined by the strap 220. For example, as illustrated in FIG. 11, the delivery assembly 240 and the strap 220 may be moved along route S to pass the delivery assembly 240 and the strap 220 through the opening 221 defined by the strap 220. Thus, the strap is looped around the bodily tissue BT as illustrated in FIG. 12.

In some embodiments, the delivery assembly 240 is sufficiently long to extend to a location outside of the patient. The delivery assembly 240 and strap 220 can then be threaded through an opening 212 defined by the support member 210. The support member 210 can then be slid along the delivery assembly 240 and strap 220 until it reaches the appropriate location on the strap 220. The delivery assembly 240 can then be removed from the strap 220 to couple the support member 210 to the strap 220 and the strap to the bodily tissue.

In some embodiments, more than one strap is used to couple the implant 200 within the body of the patient. In some embodiments, the straps are placed using the same type of coupling to the support member and to the bodily tissue. In other embodiments, the different straps are coupled to the support member and/or to the bodily tissue using different methods. For example, one strap may be looped around the support member to couple the strap to the support member, while another strap is coupled to the support member but is not looped around the support member. Similarly, one strap may be looped around bodily tissue to couple the strap to the bodily tissue, while another strap is coupled to bodily tissue but is not looped around the bodily tissue.

Figure 13:
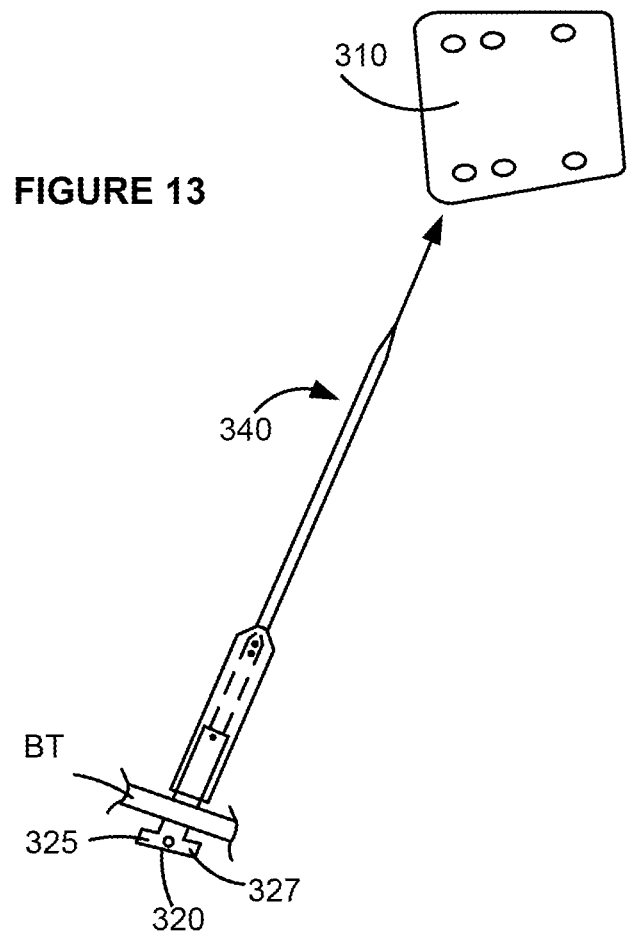
FIG. 13 illustrates a strap of an implant extending through bodily tissue.
Figure 14:
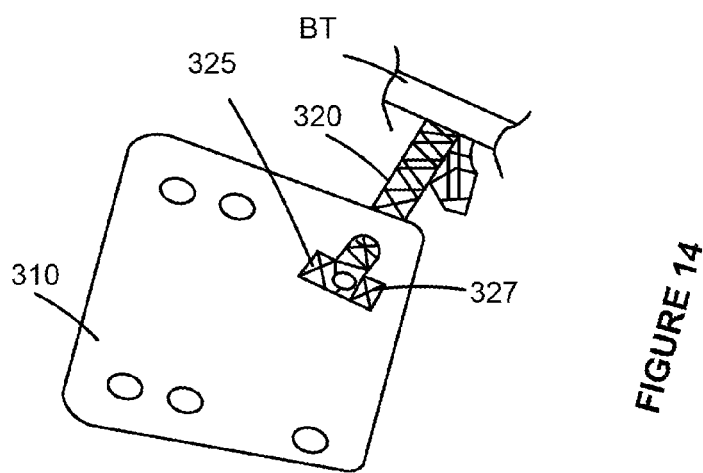
FIG. 14 illustrates the implant of FIG. 13 coupled to bodily tissue.

As illustrated in FIGS. 13 and 14, in one embodiment, a strap 320 includes extensions 325 and 327 that extend away from the longitudinal axis defined by the strap 320. Accordingly, the strap 320 has a "T" shape. As discussed above, the strap 320 may be placed within the body of a patient using a delivery assembly 340 and a delivery device.

As illustrated in FIG. 13, in one embodiment, the extensions 325 and 327 of the strap 320 may help prevent the strap 320 from pulling out of the bodily tissue BT. As illustrated in FIG. 14, in one embodiment, the extensions 325 and 327 of the strap 320 may help couple the strap 320 to a support member 310.

Although strap 320 only includes extensions on one end portion, in other embodiments, the strap includes extensions on both end portions of the strap. In such embodiments, the one set of extensions are configured to help prevent the strap from pulling out of the bodily tissue and another set of extensions are configured to help couple the strap to the support member. As illustrated in FIG. 14, the strap 320 is coupled to a support member 310 and to bodily tissue BT.

Figure 15:
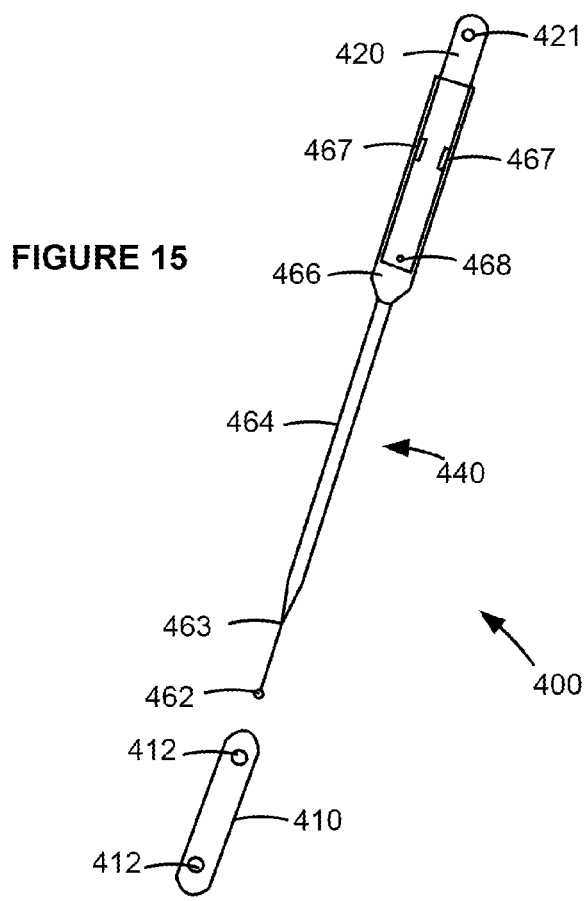
FIG. 15 illustrates an implant according to an embodiment.

FIG. 15 is a perspective view of another implant 400. The implant includes a support member 410 and a strap 420. In some embodiments, the support member 410 is an incontinence sling. In some embodiments, the support member 410 is a biologic, absorbable mesh. In other embodiments, the support member 410 is another biocompatible material. The support member 410 defines openings 412 that are configured to receive a portion of the strap 420. Although only one strap 420 is illustrated, two or more straps may be used.

The strap 420 may be coupled to the support member 410 as described above. Specifically, in one embodiment, the strap 420 extends through the opening and engages the support member 410 to couple the strap 420 to the support member 410. In another embodiment, the strap 410 is looped around the support member 410 and passed through opening 421 to couple the strap 420 to the support member 410.

The strap 420 may be associated or coupled to a delivery assembly 440 for delivery into the body of the patient. The delivery assembly 440 includes a loop 462, a leader 463, a dilator 464, a sleeve 466, and a tack 468. In one embodiment, the loop 462 is a wire loop and may be used to couple the delivery assembly 440 to a delivery device (such as a delivery device that includes a slot for receiving the wire loop). For example, in one embodiment, the delivery device is an Obtryx® device as sold by Boston Scientific Corporation. In another embodiment, the delivery device is a Lynx® device as sold by Boston Scientific Corporation.

Once the sling 420 is coupled to the support member 410 and passed through the relevant bodily tissue, the delivery assembly 440 may be removed from the strap 420 by cutting the sleeve 466 and the strap 420 at a location between the tack 468 and the opening 421 defined by the strap 420. In one embodiment, the sleeve includes two windows or slots 467. Thus, one wall of the sleeve and the strap 420 may be cut to allow the removal of the sleeve 466 from the strap 420 in a single piece.

In one embodiment, the strap 420 is delivered through the obturator membrane of the patient (a transobturator approach). In such an embodiment, an Obtryx® device may be used to deliver the strap 420. In another embodiment, the strap 420 is delivered using a supra-pubic approach. In such an embodiment, a Lynx® device may be used to deliver the strap 420.

In another embodiment, the delivery assembly includes a delivery tube rather than a dilator 464 and loop 462. In such an embodiment, the strap may be delivered using a retro-pubic approach or a pre-pubic approach. For example, in one embodiment the delivery tube may be configured to be associated with an Advantage Fit™ delivery device as sold by Boston Scientific. In such an embodiment, the strap may be delivered using a retro-pubic approach. In another embodiment, the delivery tube is configured to be associated with a Prefix delivery device as sold by Boston Scientific. In such an embodiment, the strap may be delivered using a pre-pubic approach. In some embodiments, the delivery devices include a slot configured to accept or receive the delivery assembly.

Figure 16:
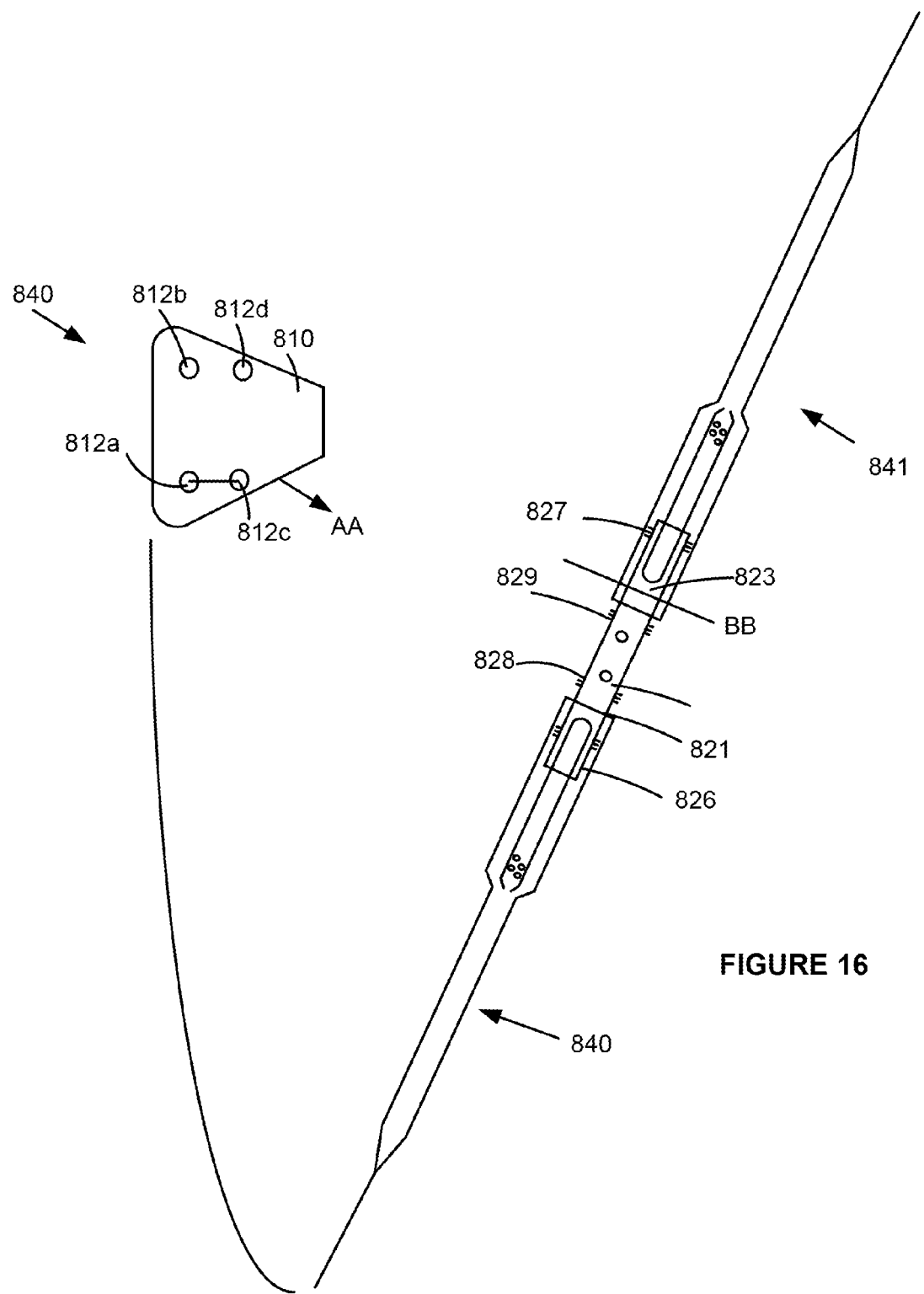
FIGS. 16 and 17 are a top views of an implants according to embodiments.

FIG. 16 is a top view of an implant 800 according to an embodiment of the invention. The implant 800 includes a support member 810 and a strap 820. The support member 810 defines several openings 812a, 812b, 812c, and 812d. The strap 820 includes a first portion 821 that has a first retention member 828 and a second retention member 826. The strap 820 also includes a second portion 823 that has a first retention member 827 and a second retention member 829.

The retention members 828 and 829 are configured to engage and be coupled to the support member 810. The retention member 826 and 827 are configured to engage and couple to portions of the body of the patient, such as bodily tissue. The implant 800 also includes delivery assemblies 840 and 841 coupled to the first portion 821 and the second portion 823 of the strap 820, respectively. The delivery assemblies 840 and 841 are configured to facilitate the placement of the strap 820 within the body of the patient.

As illustrated in FIG. 16, the strap 820 may be threaded through two of the openings defined by the support member 810. For example, the strap 820 may be moved along path AA to be threaded or pass through openings 812a and 812c along one side of the support member 810. The end portions 823 and 824 of the strap 820 may then be passed through or coupled to different portions of the body of the patient. For example, in one embodiment, one end portion may be coupled to the sacrospinous ligament of the patient and the other end portion may be coupled to the arcus tendineus of the patient.

In another embodiment, the strap 820 may be threaded through a single opening defined by the support member 810 and both portions 821 and 823 of the strap 820 may be coupled to different portions of the body of the patent.

In one embodiment, the strap 820 is cut, for example, along line BB to form a longer strap.

Figure 17:
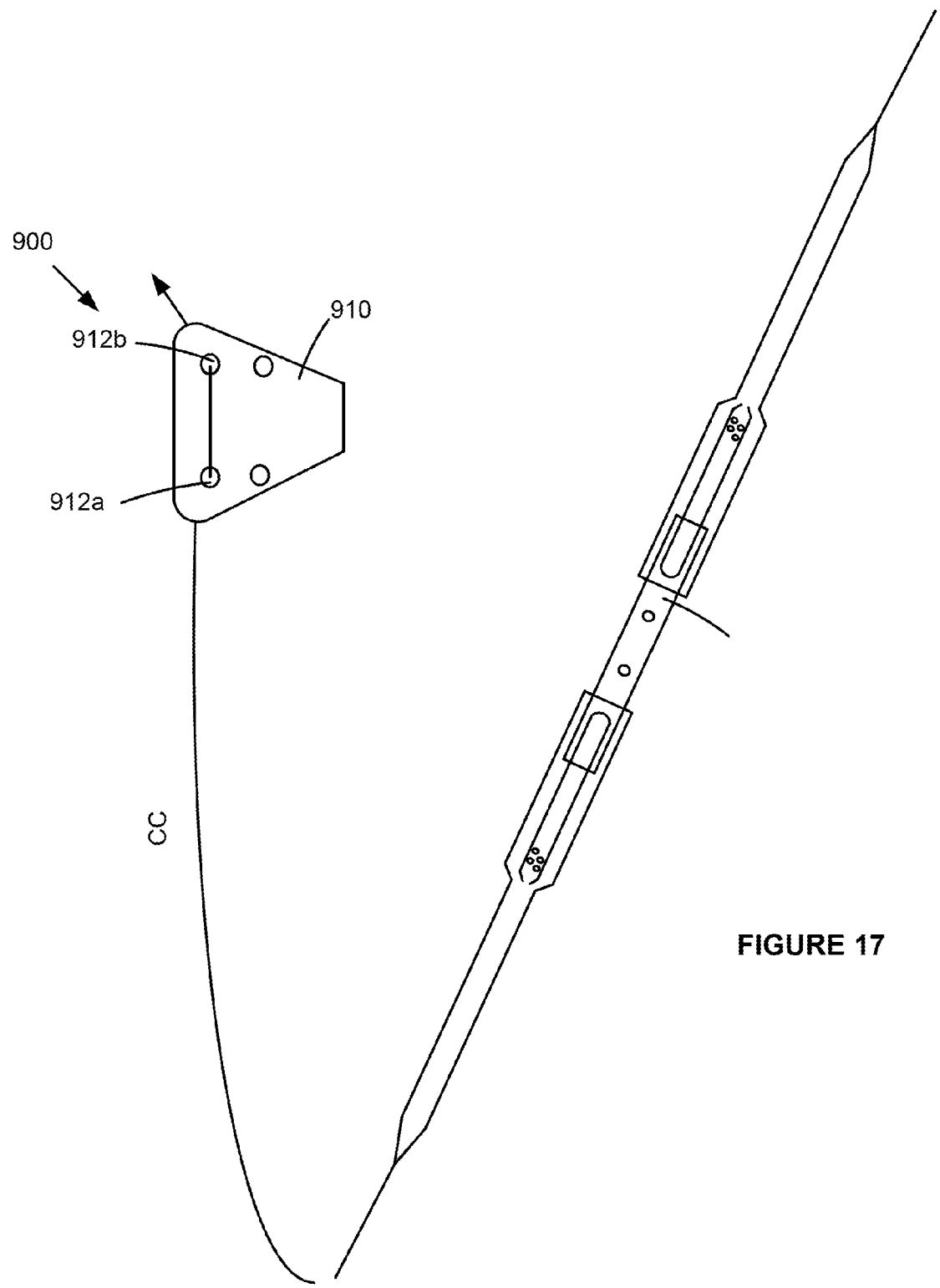

As best illustrated in FIG. 17, in one embodiment, a strap 920 of an implant 900 may be moved along path BB to be threaded or pass through openings 912a and 912b along one end of a support member 910.

In some embodiments, the support member is formed of a biologic material and the strap is formed of a absorbable material or mesh.

Figure 20:
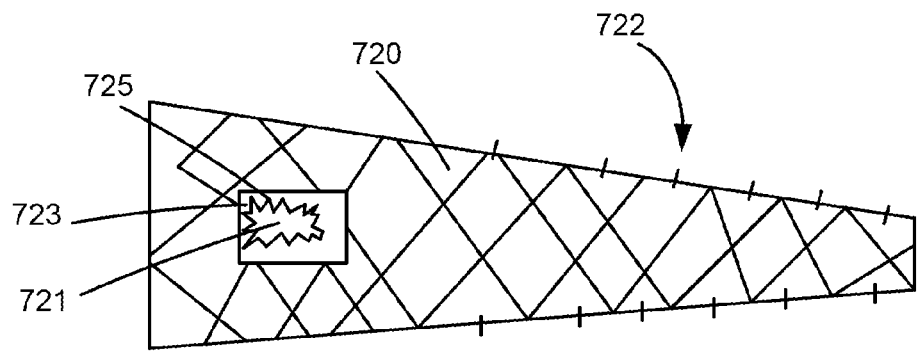
FIGS. 18-20 are top views of straps according to embodiments.
Figure 19:
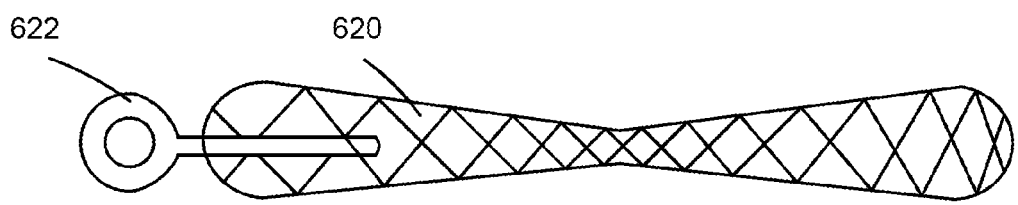
Figure 18:
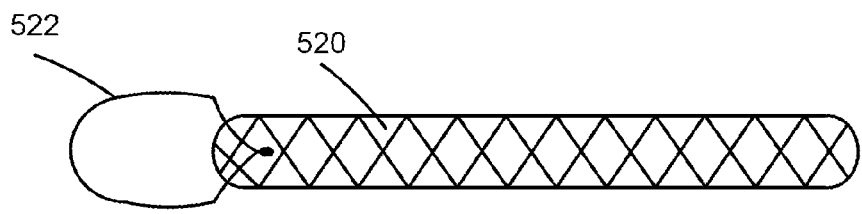

FIGS. 18-20 are top views of straps according to embodiments of the invention. As illustrated in FIG. 18, the strap 520 includes an association loop 522. The association loop 522 may be used to loop the strap 520 around a support member and/or bodily tissue to couple the strap 520 to the support member and/or to bodily tissue as described above. In one embodiment, the loop 522 is a suture loop. In one embodiment, the loop 522 formed of an absorbable suture.

As illustrated in FIG. 19, the strap 620 may have an hourglass shape and may include a molded association loop 622. The molded association loop 622 may be coupled to the strap 620 using any known means for coupling such items. In some embodiments, the association loop 622 is made of polypropylene.

As illustrated in FIG. 20, the strap 720 has a triangular shape and includes reinforced portions. Specifically, the strap 720 includes a reinforced retention member 722. In such an embodiment, the reinforced retention member 722 helps couple the strap to a support member or to bodily tissue. In some embodiments, the reinforced retention member 722 is a set of tangs that include a reinforcement material. In some embodiments, the reinforcement material is polypropylene.

The strap 720 also defines a reinforced opening 721. The reinforced opening 721 includes a reinforcement material and is configured to grip the portion of the strap 720 that extends through the opening 721. In some embodiments, the reinforced opening 721 includes a molded portion 723. In some such embodiments and as illustrated in FIG. 18, the molded portion 723 includes extensions or teeth 725 to help couple the molded portion 723 to the portion of the strap 720 that extends through the opening 721. Opening 721 can be formed by heat cutting or laser cutting.

In one embodiment, an implant comprises a support member defining an opening, and a strap being configured to extend through the opening defined by the support member. The strap includes a first retention member and a second retention member. The first retention member is configured to engage the support member to couple the strap to the support member. The second retention member is configured to engage bodily tissue of a patient to couple the strap to the bodily tissue.

In one embodiment, the strap and the first retention member are monolithically formed. In another embodiment, the strap and the second retention member are monolithically formed. In one embodiment, the first retention member includes at least one tang. In another embodiment, the second retention member includes at least one tang.

In one embodiment, the strap defines a longitudinal axis and the first retention member extends away from the longitudinal axis defined by the strap. In another embodiment, the strap defines a longitudinal axis and the second retention member extends away from the longitudinal axis defined by the strap. In one embodiment, the strap defines an opening and the strap is configured to extend through the opening defined by the strap.

In some embodiments, the strap is formed of a mesh material. In other embodiments, the strap includes a mesh portion and a molded portion. In some embodiments, the strap includes a mesh portion and a molded portion and the molded portion includes a plurality of teeth. In some embodiments, the strap includes a mesh portion and a molded portion and the molded portion extends from an end portion of the mesh portion. In some embodiments, the strap includes a mesh portion and a suture loop.

In one embodiment, an implant comprises a support member defining an opening and a strap defining an opening and being configured to be coupled to the support member and to bodily tissue of a patient. The strap is configured to extend through the opening defined by the support member and the opening defined by the strap.

In some embodiments, the strap includes mesh portion and a molded portion. In other embodiments, the strap includes a mesh portion and a molded portion and the molded portion extends from an end portion of the mesh portion.

In some embodiments, the strap includes a retention member configured to couple the strap to the support member. In some embodiments, the strap includes a retention member configured to couple the strap to the bodily tissue of the patient.

In one embodiment, a method of placing an implant within a body of a patient comprises extending a strap through an opening defined by a support member, extending the strap through bodily tissue of the patient, and extending the strap through an opening defined by the strap. In some embodiments, the extending the strap through an opening defined by the strap includes extending the strap through an opening defined by the strap after the extending a strap through an opening defined by a support member and after the extending the strap through bodily tissue of the patient.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. An implant for a pelvic floor dysfunction, comprising:
a support member defining an opening between a central axis of the support member and an edge of the support member; and
a strap being configured to extend through the opening defined by the support member, the strap including a first retention member, a second retention member, and a middle portion disposed between the first retention member and the second retention member, the first retention member being configured to engage the support member to couple the strap to the support member, the second retention member being configured to engage bodily tissue of a patient to couple the strap to the bodily tissue, the strap having a mesh material,
wherein the first retention member includes a first set of tangs defined by the mesh material on a proximal end portion of the strap, the strap being coupled to the opening defined by the support member based on an engagement of the first set of tangs with the support member, the second retention member includes a second set of tangs defined by the mesh material on a distal end portion of the strap, and the middle portion disposed between the first set of tangs and the second set of tangs devoid of tangs,
the first set of tangs being disposed a distance from a proximal terminal end of the strap, and a portion between the proximal terminal end and the first set of tangs is devoid of tangs.

2. The implant of claim 1, wherein the strap and the first and second retention members are monolithically formed.

3. The implant of claim 1, wherein the opening defined by the support member is round.

4. The implant of claim 1, wherein the strap defines a longitudinal axis, the first and second retention members extending away from the longitudinal axis defined by the strap.

5. The implant of claim 1, wherein the mesh material of the strap is an absorbable material.

6. The implant of claim 1, wherein the strap defines an opening, the strap being configured to extend through the opening defined by the strap.

7. The implant of claim 1, wherein the strap includes a molded portion.

8. The implant of claim 1, wherein the strap includes a molded portion, the molded portion includes a plurality of teeth.

9. The implant of claim 1, wherein the strap includes a molded portion, the molded portion extending from an end portion of the mesh portion.

10. The implant of claim 1, wherein the opening includes a plurality of openings disposed on a first side portion of the support member and a plurality of openings disposed on a second side portion, the central axis of the support member being disposed between the first side portion and the second side portion.

11. The implant of claim 1, wherein the first set of tangs are configured to engage the support member such that the engagement frictionally couples the strap to the support member.

12. The implant of claim 1, wherein the first set of tangs are reinforced tangs having a reinforcement material added to the first set of tangs.

13. The implant of claim 12, wherein the reinforcement material includes polypropylene.

14. The implant of claim 1, wherein the second set of tangs is disposed a distance from a distal terminal end of the strap, and the mesh material between the distal terminal end of the strap and the second set of tangs is devoid of tangs.

15. An implant for treatment of a pelvic dysfunction, comprising:
a support member defining an opening between a central axis of the support member and an edge of the support member; and
a strap defining an opening and being configured to be coupled to the support member and to bodily tissue of a patient, the strap including a mesh material,
the strap including a first set of tangs defined by the mesh material on a proximal end portion of the strap and a second set of tangs defined by the mesh material on a distal end portion of the strap, the strap including a middle portion between the first set of tangs and the second set of tangs, the middle portion being devoid of tangs,
the first set of tangs being disposed a distance away from a proximal terminal end of the strap such that the mesh material between the proximal terminal end and the first set of tangs is devoid of tangs, the second set of tangs being disposed a distance from a distal terminal end of the strap such that the mesh material between the distal terminal end and the second set of tangs is devoid of tangs.

16. The implant of claim 15, wherein the opening of the strap includes a molded portion having a different material than the mesh material of the strap.

17. The implant of claim 16, wherein the opening includes three openings disposed on a first side portion of the support member and three openings disposed on a second side portion, the central axis of the support member being disposed between the first side portion and the second side portion.

18. The implant of claim 15, wherein the first set of tangs are configured to engage the support member such that the engagement frictionally couples the strap to the support member.

19. A method of placing an implant within a pelvic region of a patient, comprising:
- extending a strap through an opening defined by a support member;
- extending the strap through bodily tissue of the patient such that the strap extends from one side of the bodily tissue, through the bodily tissue, to the other side of the bodily tissue; and
- extending the strap through an opening defined by the strap such that a portion of the strap extends on one side of the support member and another portion of the strap extends on the other side of the support member,
- wherein the extending the strap through the opening defined by the strap includes extending the strap through the opening defined by the strap after the extending the strap through the opening defined by the support member and after the extending the strap through the bodily tissue of the patient,
- wherein the strap is looped around both the support member and the bodily tissue.

* * * * *